US00PP19867P2

(12) United States Plant Patent
Warren et al.

(10) Patent No.: US PP19,867 P2
(45) Date of Patent: Mar. 31, 2009

(54) CALLA LILY PLANT NAMED 'MERLOT BLZ'

(50) Latin Name: ***Zantedeschia* sp.**
Varietal Denomination: Merlot BLZ

(75) Inventors: Andrew G. F. Warren, Tauranga (NZ); Jacobus P. Spaans, Tauranga (NZ)

(73) Assignee: BLOOMZ Ltd, Tauranga (NZ)

( * ) Notice: Subject to any disclaimer, the term of this patent is extended or adjusted under 35 U.S.C. 154(b) by 0 days.

(21) Appl. No.: 12/148,594

(22) Filed: Apr. 21, 2008

(51) Int. Cl.
*A01H 5/00* (2006.01)

(52) U.S. Cl. ..... Plt./490
(58) Field of Classification Search ..... Plt./490
See application file for complete search history.

*Primary Examiner*—Kent L Bell
(74) *Attorney, Agent, or Firm*—Jondle & Associates, P.C.

(57) ABSTRACT

A calla lily plant particularly distinguished by red-purple spathes, medium-density maculation on the upper surface of the leaves that is visible from the lower surface and produces 2 to 4 inflorescences per 3-cm tuber, is described.

3 Drawing Sheets

Genus and species: *Zantedeschia* sp.
Variety denomination: 'Merlot BLZ'.

BACKGROUND OF THE NEW PLANT

The present invention comprises a new and distinct cultivar of calla lily, botanically known as *Zantedeschia* sp., and hereinafter referred to by the cultivar name 'Merlot BLZ'. The new cultivar was asexually reproduced from micropropagation by tissue culture resulting from the cross of the female parent 'Majestic Red', an unpatented *Zantedeschia* variety and the male parent, an unnamed, unpatented *Zantedeschia* variety having pink spathes. 'Merlot BLZ' is a product of a planned breeding program intended to create new calla lily plants with dark red-purple spathes.

The new cultivar was created in Tauranga, New Zealand and has been asexually reproduced repeatedly from micropropagation by tissue culture in New Zealand over a three year period. The present invention has been found to retain its distinctive characteristics through successive propagations.

Plant Breeder's Rights for this cultivar were applied for in Australia on Apr. 19, 2007, in New Zealand on May 3, 2007 and with the European Union on Oct. 29, 2007. 'Merlot BLZ' has not been made publicly available more than one year prior to the filing date of this application.

SUMMARY OF THE INVENTION

The following are the most outstanding and distinguishing characteristics of this new cultivar when grown under normal horticultural practices in Tauranga, New Zealand.

1. Red-purple spathes;
2. Medium-density maculation of the leaves on the upper surface that is visible from the lower surface; and
3. Produces 2 to 4 inflorescences per 3-cm tuber.

DESCRIPTION OF THE PHOTOGRAPHS

This new calla lily plant is illustrated by the accompanying photographs which show the plant habit, mature inflorescence and foliage of the plant. The colors shown are as true as can be reasonably obtained by conventional photographic procedures. The plants in the photographs are seven to eight weeks-old.

DESCRIPTION OF THE NEW CULTIVAR

Figure 1:
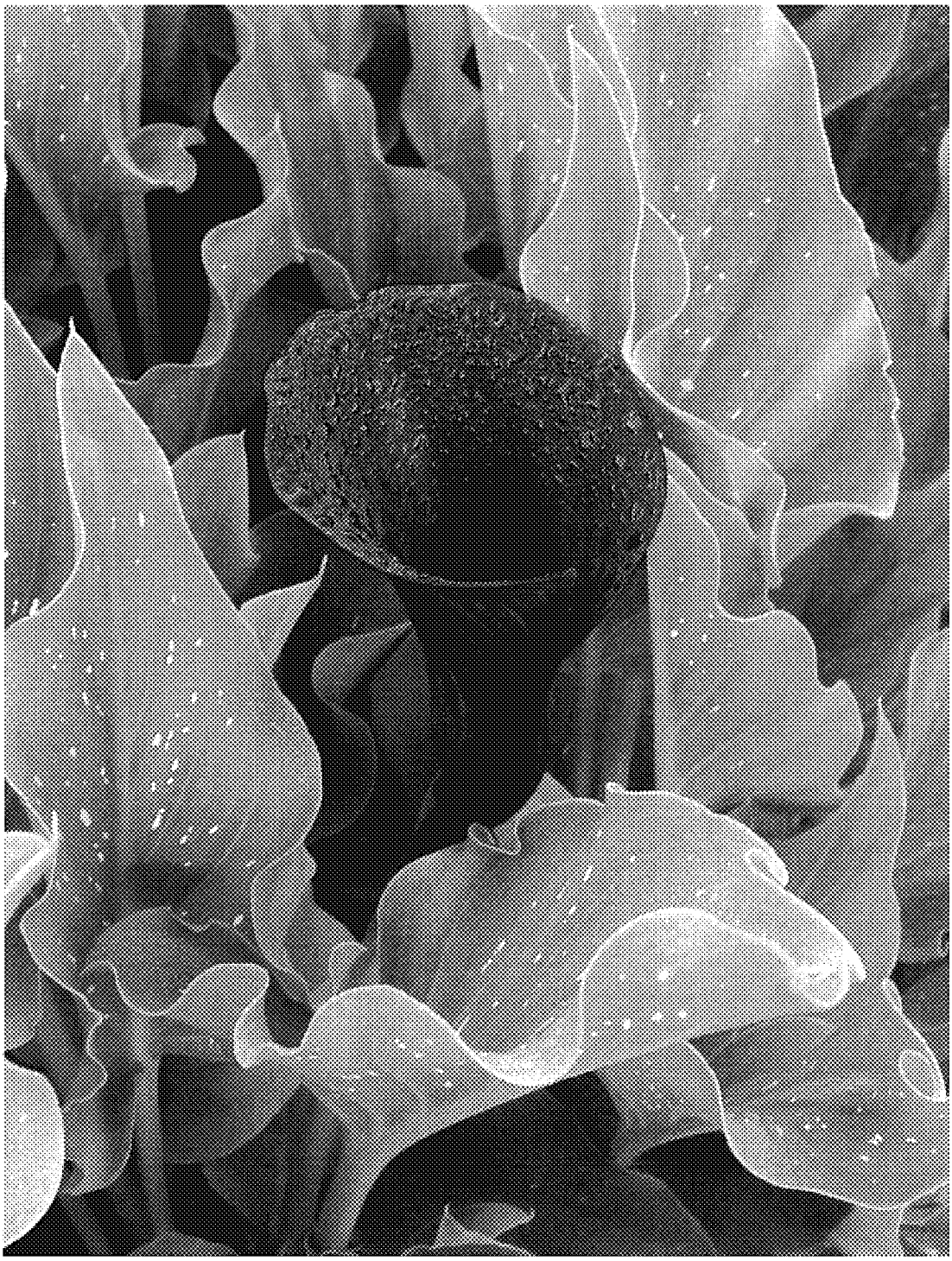
FIG. 1 shows the mature inflorescence and foliage.
Figure 2:
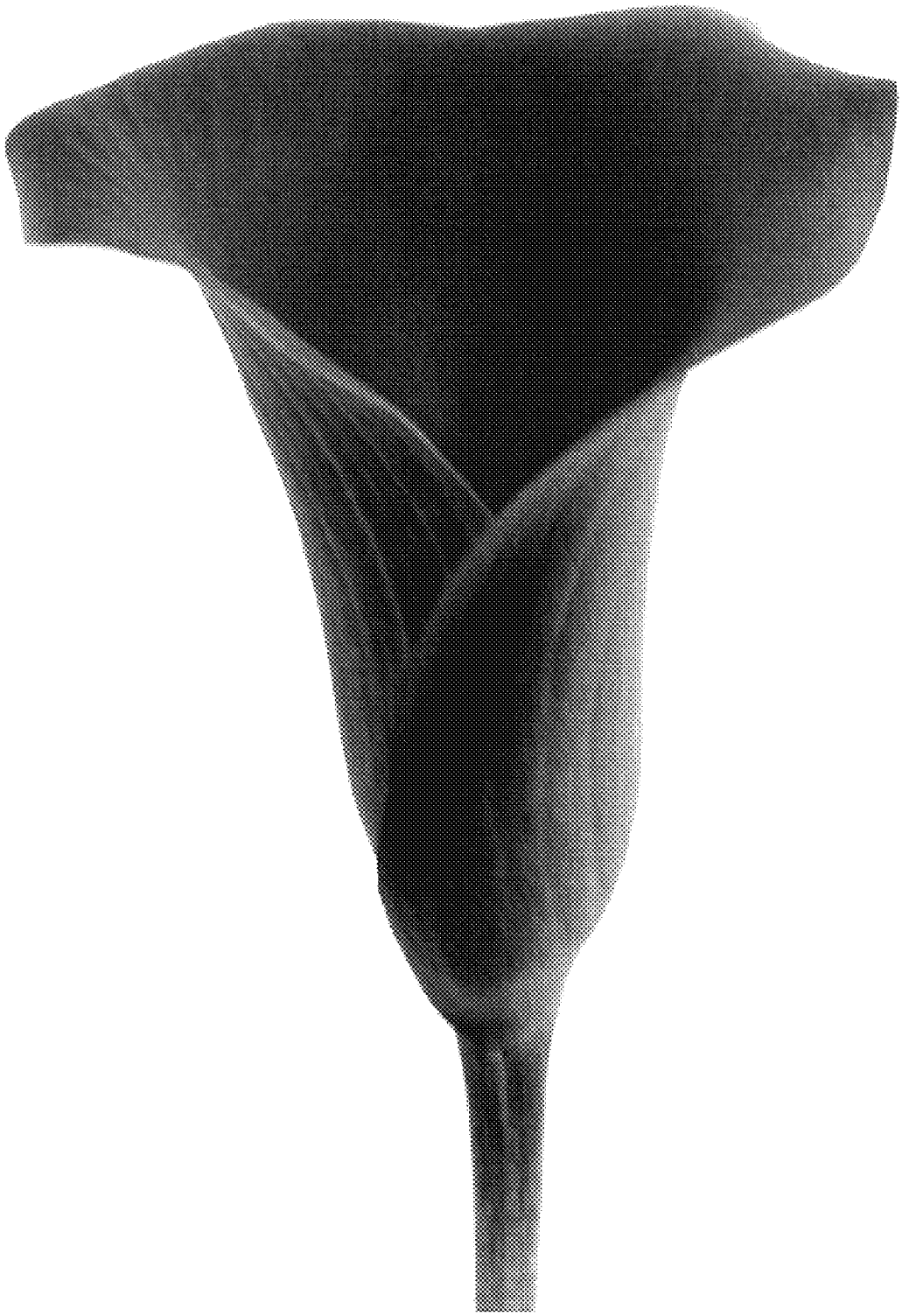
FIG. 2 shows a close-up of the mature inflorescence.
Figure 3:
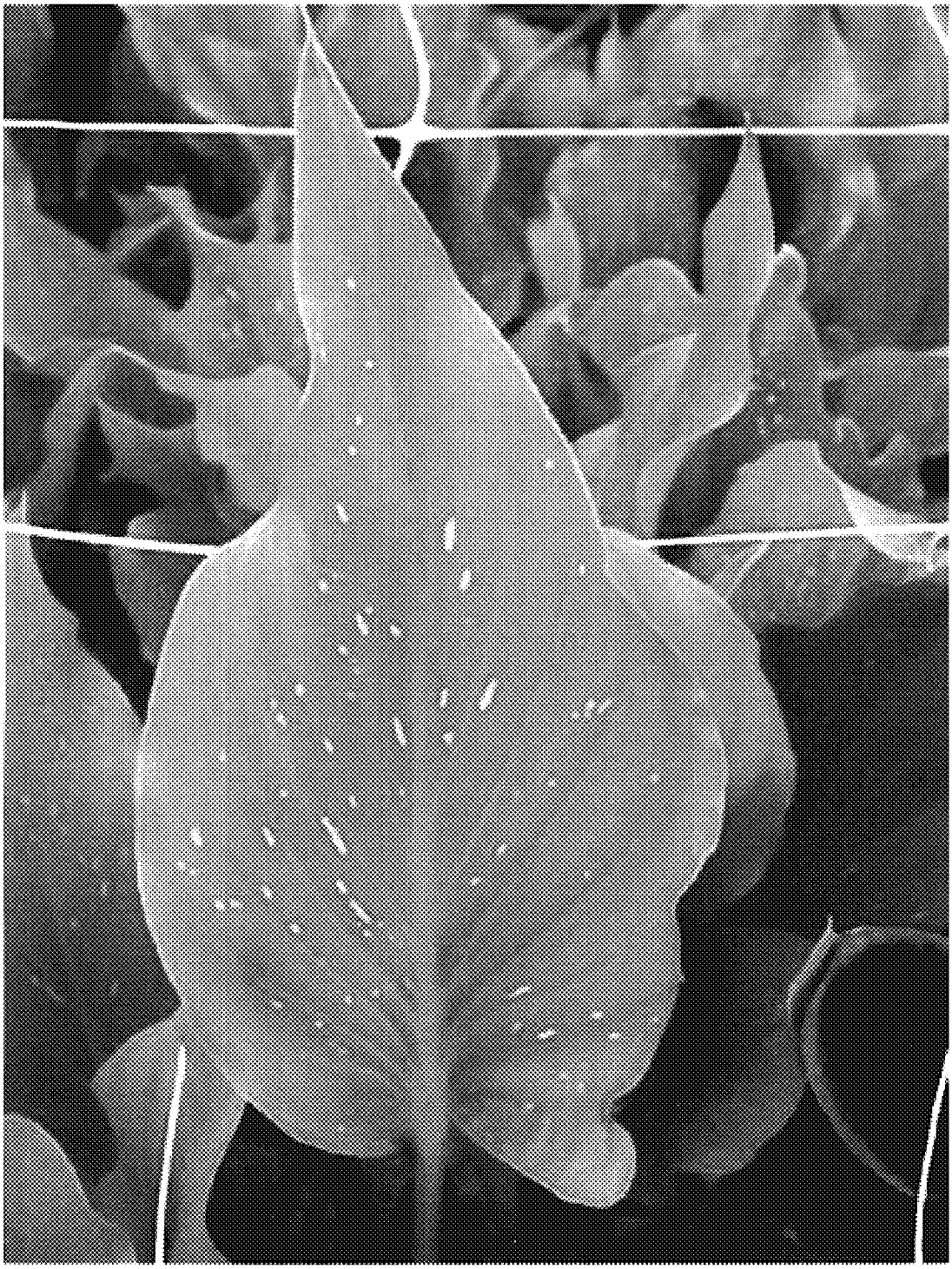
FIG. 3 shows a close-up of the leaf and maculation.

The following detailed description sets forth the distinctive characteristics of 'Merlot BLZ'. The data that define these characteristics were collected from asexual reproductions carried out in New Zealand. The plant history was taken on plants of two-year-old tubers based on a 3-cm diameter tuber under New Zealand summer conditions. Color references are primarily to the R.H.S. Colour Chart of The Royal Horticultural Society of London (R.H.S.).

DETAILED BOTANICAL DESCRIPTION

Classification:
- *Family.*—Araceae.
- *Botanical name.*—*Zantedeschia* sp.
- *Common name.*—Calla lily.

Parentage:
- *Female parent.*—'Majestic Red', an unpatented *Zantedeschia* variety having red spathes.
- *Male parent.*—An unnamed, unpatented *Zantedeschia* variety having pink spathes.

Plant:
- *Form.*—Erect.
- *Height of the leaf canopy above the soil.*—35 cm to 50 cm.
- *Height of top of inflorescence above the soil.*—40 cm to 55 cm.
- *Diameter.*—20 cm to 35 cm.
- *Number of inflorescences per tuber size.*—Tuber diameter 3 cm: 2 to 4. Tuber diameter 4 cm: 3 to 5. Tuber diameter 5 cm: 5+.
- *Time to produce a finished flowering plant.*—6 to 10 weeks depending on the climate and environment.
- *Lastingness of the inflorescence on the plant.*—2 to 3 weeks.

Leaves:

*Size.*—Length: 16 cm to 20 cm. Width: 8 cm to 12 cm.

*Shape.*—Ovate towards sagittate (arrow-shaped).

*Apex.*—Acute to apiculate.

*Margin.*—Moderately wavy.

*Margin color.*—RHS 144B (yellow-green).

*Venation patter.*—Pinnate.

*Surface texture.*—Leathery.

*Color.*—Upper surface: RHS 137A. Lower surface: RHS 137B.

*Maculation* (*leaf spots*).—General: Maculation is only on the upper surface of the leaf but is visible from the lower surface. Density: Medium density. Color: RHS 155C.

*Petiole.*—Average number per tuber: 1 to 3. Length: 15 cm to 30 cm. Diameter: 0.6 cm to 1 cm. Texture: Smooth. Character: Strong. Color: Base: RHS 155A. Lower portion: RHS 146B. Upper portion: RHS 144A. Sheath: Length: 4 cm to 8 cm. Diameter: 1.0 cm to 1.6 cm. Color: RHS 146B (yellow-green).

Roots:

*Color.*—RHS 155D (white).

*Branching.*—Not branched, attached to the top of the tuber at the apices.

Inflorescence:

*Spathe* (*flower body*).—Size: Height: 8 cm to 10 cm. Width: 5.5 cm to 6.5 cm. Color (both upper and lower parts): RHS 59A. Vein color: RHS 60A. Fragrance: Absent. Shape: Cup-shaped. Texture: Smooth. Apex: Cuspidate. Base: Attenuate. Margin: Entire.

*Spadix* (*reproductive organs*).—Size: Length: 2.0 cm to 2.5 cm. Diameter: 0.4 cm to 0.7 cm. Color: Base: RHS 59A. Upper part: RHS 39A. Position relative to spathe: Upright. Shape: Elongated. Apex: Rounded.

*Peduncle* (*flower stem*).—Length: 35 cm to 55 cm. Diameter: 0.5 cm to 0.7 cm. Color: Base: RHS 155A. Upper part: RHS 144A. Surface texture: Smooth. Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Pollen color.*—RHS 155A (white).

*Stamens.*—Not visible before pollen release.

*Pistil.*—Number: 20 to 30 per spadix. Color: RHS 17B.

Fruit (berries):

*Quantity of berries per plant.*—10 to 20.

*Color.*—RHS 145B.

*Size.*—Length: 0.6 cm to 0.8 cm. Width: 0.6 cm to 0.8 cm.

Disease and insect resistance:

*Disease resistance.*—No susceptibility noted to date.

*Pest resistance.*—No susceptibility noted to date.

COMPARISON WITH PARENTAL AND KNOWN CULTIVARS

When compared to the female parent, 'Majestic Red' (unpatented), 'Merlot BLZ' has a larger number and more uniform inflorescences and a thinner peduncle than 'Majestic Red'.

When compared to the male parent, an unnamed unpatented individual *Zantedeschia* variety, 'Merlot BLZ' has red-purple spathes, while the male parent has pink spathes.

When compared to the commercial variety 'Vermeer' (U.S. Plant Pat. No. 18,281) in that 'Merlot BLZ' has red-purple spathes, while 'Vermeer' has white and purple spathes.

We claim:

1. A new and distinct cultivar of calla lily plant as shown and described herein.

* * * * *